(12) United States Patent
Chen

(10) Patent No.: US 7,527,778 B2
(45) Date of Patent: May 5, 2009

(54) ZINC-CONTAINING ZEOLITE WITH IFR FRAMEWORK TOPOLOGY

(75) Inventor: Cong-Yan Chen, Kensington, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 146 days.

(21) Appl. No.: 11/759,849

(22) Filed: Jun. 7, 2007

(65) Prior Publication Data

US 2007/0292343 A1 Dec. 20, 2007

Related U.S. Application Data

(60) Provisional application No. 60/805,011, filed on Jun. 16, 2006.

(51) Int. Cl.
 *C01B 39/04* (2006.01)
(52) U.S. Cl. .................. 423/326; 423/331; 423/332; 423/333; 423/706
(58) Field of Classification Search ............. 423/326, 423/331, 332, 333, 706
See application file for complete search history.

(56) References Cited

U.S. PATENT DOCUMENTS

| | | | |
|---|---|---|---|
| 3,140,249 A | 7/1964 | Plank et al. | |
| 3,140,251 A | 7/1964 | Plank et al. | |
| 3,140,253 A | 7/1964 | Plank et al. | |
| 3,709,853 A | 1/1973 | Karapinka | |
| 3,852,207 A | 12/1974 | Stangeland et al. | |
| 3,894,107 A | 7/1975 | Butter et al. | |
| 3,904,513 A | 9/1975 | Fischer et al. | |
| 3,960,978 A | 6/1976 | Givens et al. | |
| 4,086,408 A | 4/1978 | Karol et al. | |
| 4,157,294 A | 6/1979 | Iwao et al. | |
| 4,181,598 A | 1/1980 | Gillespie et al. | |
| 4,297,328 A | 10/1981 | Ritscher et al. | |
| 4,347,121 A | 8/1982 | Mayer et al. | |
| 4,376,722 A | 3/1983 | Chester et al. | |
| 4,377,497 A | 3/1983 | Chester et al. | |
| 4,446,243 A | 5/1984 | Chester et al. | |
| 4,526,942 A | 7/1985 | Chester et al. | |
| 4,734,537 A | 3/1988 | Devries et al. | |
| 4,810,357 A | 3/1989 | Chester et al. | |
| 4,910,006 A | 3/1990 | Zones et al. | |
| 4,921,594 A | 5/1990 | Miller | |
| 4,939,311 A | 7/1990 | Washecheck et al. | |
| 4,962,261 A | 10/1990 | Abrevaya et al. | |
| 5,095,161 A | 3/1992 | Abrevaya et al. | |
| 5,105,044 A | 4/1992 | Han et al. | |
| 5,105,046 A | 4/1992 | Washecheck | |
| 5,149,421 A | 9/1992 | Miller | |
| 5,238,898 A | 8/1993 | Han et al. | |
| 5,316,753 A | 5/1994 | Nakagawa | |
| 5,321,185 A | 6/1994 | van der Vaart | |
| 5,336,825 A | 8/1994 | Choudhary et al. | |
| 5,437,855 A | 8/1995 | Valyocsik | |
| 5,441,721 A | 8/1995 | Valyocsik | |
| 5,653,956 A | 8/1997 | Zones | |
| 6,117,411 A | 9/2000 | Takewaki et al. | |
| 6,468,501 B1 | 10/2002 | Chen et al. | |
| 6,790,433 B2 | 9/2004 | Chen et al. | |
| 2007/0098630 A1* | 5/2007 | Chen | 423/706 |

OTHER PUBLICATIONS

Williams, "Zeolites", Encyclopedia of Inorganic Chemistry, (2006).*
Chen et al, "Synthesis and characterization of zincosilicate and pue-silica SSZ-42 and SSZ-71", From Zeolites to Porous MOF Materials, (2007).*
P. A. Barrett, et al., Structure of ITQ-4, a New Pure Silica Polymorph Containing Large Pores and a Large Void Volume, Chemistry of Materials, Aug. 1997, Paper No. S0897-4756(97)00173-7, pp. 1713-1715, vol. 9, Issue 8, American Chemical Society, Washington, D. C.
S. Hamoudi, et al., Synthesis and Characterization of Titanium-Substituted Large Pore SSZ-42 Zeolite, Catalysis Letters, Dec. 2001, Paper No. 1011-372X/01/1200-0227, pp. 227-231, vol. 77, No. 4, Springer Netherlands, Rotterdam, The Netherlands.
G. Kosova, et al., Synthesis of MCM-58: Incorporation of Aluminum and Iron Into Framework Positions, Proceedings: 14th International Zeolite Conference, Cape Town, South Africa, Apr. 25-30, 2004, ISBN: 0-958-46636-X, pp. 863-869, M-Cam, Inc., Arlington, Virginia.

* cited by examiner

*Primary Examiner*—David M Brunsman
(74) *Attorney, Agent, or Firm*—Richard J. Sheridan

(57) ABSTRACT

A process is disclosed for preparing a zinc-containing molecular sieve having IFR framework topology and having zinc atoms in its crystal framework, said process comprising:

(a) preparing an aqueous mixture containing sources of silicon oxide, zinc oxide, an alkali metal, and an N-benzyl-1,4-diazabicyclo[2.2.2]octane cation having an anionic counterion which is not detrimental to the formation of the molecular sieve; and (b) maintaining the aqueous mixture under conditions sufficient to form crystals of the molecular sieve.

4 Claims, No Drawings

ZINC-CONTAINING ZEOLITE WITH IFR FRAMEWORK TOPOLOGY

This application claims the benefit under 35 USC 119 of U.S. Provisional Application 60/805,011, filed Jun. 16, 2006.

Zeolites are an important class of microporous, crystalline solids which are used industrially in heterogeneous catalysis, adsorption, separation and ion-exchange. The properties of zeolites for these applications are strongly affected by the structural features such as the framework composition and topology In this invention, we discovered a new zincosilicate zeolite with the framework structure designated IFR by the International Zeolite Association.

Today over 170 zeolite structures have been discovered. Theoretical studies indicate, however, that this number represents only a small fraction of the structures possible for microporous, crystalline molecular sieves. The major roadblock in tailoring and utilizing zeolites for specific applications remains the development of synthesis methods to produce desirable structures with desirable framework composition. In principle, there are two routes to achieve this goal: (1) direct synthesis and (2) post-synthetic treatment.

The direct synthesis is the primary route of the synthesis of zeolites, The major variables that have a predominant influence on the zeolite structure crystallized include the composition of the synthesis mixture, temperature and time. Depending on the nature of the zeolites involved and the chemistry of their formation, some zeolite structures can be synthesized in a broad spectrum of framework compositions, as exemplified by ZSM-5 containing no heteroatoms (Si-ZSM-5, i.e., pure-silica ZSM-5). B-ZSM-5 (i-e., borosilicate ZSM-5), Ga-ZSM-5 (i.e., gallosilicate ZSM-5) and Al-ZSM-5 (i.e., aluminosilicate ZSM-5). By contrast, the synthesist of some other structures succeeds only if a certain heteroatom X (X=B, Ge or Al, for example) is present in the synthesis mixture and, in turn, incorporated into the framework. In many cases, certain zeolite structures can be synthesized only with certain specific heteroatoms within a limited range of Si/X ratio or in the presence of certain specific structure directing agents (SDAs). These complicated relationships between zeolite structures, framework compositions and SDAs have been discussed in many publications and patents, In addition to the direct synthesis method, post-synthetic treatments often provide an alternative route to modify the zeolites to acquire desirable framework compositions. The post-synthetic treatment techniques all operate on the same principle: the desirable atoms such as Al and Si are inserted into lattice sites previously occupied by other T-atoms such as B. For example, a method was developed of making aluminosilicate zeolites post-synthetically via treatment of borosilicate zeolites with aluminum salts (e.g., $Al(NO_3)_3$) to replace the framework boron with aluminum (see U.S. Pat. No. 6,468,501 and U.S. Pat. No. 6,790,433).

Zeolites having the IFR framework topology ("IFR zeolites") are known. U.S. Pat. No. 5,437,855, issued Aug. 1, 1995 to Valyocsik, discloses a zeolite, designated "MCM-58", having the IFR framework topology prepared using a benzylquinuclidinium organic structure directing agent. U.S. Pat. No. 5,441,721, issued Aug. 15, 1995 to Valyocsik, also discloses MCM-58, but prepared using a benzyltropanium organic structure directing agent. Both patents are incorporated by reference herein in their entirety. U.S. Pat. No. 5,653,956, issued Aug. 5, 1997 to Zones, discloses a zeolite having the IFR framework topology, designated SSZ-42, prepared using an organic structure directing agent selected from the group consisting of 1-benzyl-4-aza-1-azonia-bicyclo[2.2.2] octane cations and N-benzyl-1-azabicylo [2.2.2]octane cations. The SSZ-42 may contain oxides of boron, aluminum, gallium, iron or titanium, but at least 50% of those oxides must be boron oxide. U.S. Pat. No, 5,653,956 is incorporated herein by reference in its entirety. Another zeolite, designated ITQ-4, is also an IFR zeolite (see P. A. Barrett, M. A. Gamblor, A. Corma, R. H. Jones, L. A. Villaescusqa Chem. Mater., 1997, 9, 1713.

The present invention will now be described with respect to SSZ42, but it should be understood that it applies to other IFR zeolites, such as MCM-58 and ITQ-4.

The framework structure of zeolite SSZ-42 is characterized by an undulating, one-dimensional 12-membered ring channel system. According to the International Zeolite Association (IZA), SSZ-42, MCM-58 and ITQ-4 have the same crystalline structure. The IZA code for this structure is IFR.

SSZ-42 has been successfully synthesized in pure-silica, borosilicate and aluminosilicate form (Si-SSZ-42, B-SSZ-42 and Al-SSZ42) by using a variety of benzyl derivatives such as N-benzyl-1,4-diazabicyclo[2.2.2]octane, N-benzylquinuclidinium and N-benzylquinuclidinol cations as structure directing agents (SDAs). It has been reported that this zeolite can also be prepared in ferrosilicate and titanosilicate forms (see G. Kosova, S. Ernst, M. Hartmann and J. Cejka, Proc. 14th Intern. Zeolite Conf., Cape Town, South Africa, (2004) 863; S. Hamoudi, F. Larachi and A. Sayari, Catal. Letters, 77 (2001). 227.

SUMMARY OF THE INVENTION

The present invention relates to the synthesis of SSZ-42 having zinc atoms in its crystal framework (referred to herein as "Zn-SSZ-42", "zinc-containing SSZ-42" or "zinc containing molecular sieve having IFR framework topology") via the direct synthesis route. As used herein, lithe term "direct synthesis" means that the Zn-SSZ-42 is the product made from a reaction mixture without the necessity of preparing an intermediate form of SSZ-42 containing a hetero atom (such as B) and then replacing the heteroatom with zinc in a post-synthesis treatment.

Thus, in accordance with the present invention there is provided a process for preparing a zinc-containing molecular sieve having IFR framework topology and having zinc atoms in its crystal framework, said process comprising:

(a) preparing an aqueous mixture containing sources of silicon oxide, zinc oxide, an alkali metal, and an N-benzyl-1,4-diazabicyclo [2.2.2]octane cation having an anionic counterion which is not detrimental to the formation of the molecular sieve, and (b) maintaining the aqueous mixture under conditions sufficient to form crystals of the molecular sieve.

The present invention also provides a zinc-containing molecular sieve having IFR framework topology and having a composition, as synthesized and in the anhydrous state, in terms of mole ratios as follows:

| | |
|---|---|
| $YO_2/ZnO$ | 10-200 |
| $M_{2/n}/YO_2$ | 0-0.03 |
| $Q/YO_2$ | 0.02-0.05 | wherein Y is silicon, germanium or mixtures thereof; M is an alkali metal cation, alkaline earth metal cation or mixtures thereof; n is the valence of M (i.e., 1 or 2); and Q is an N-benzyl-1,4-diazabicyclo[2.2.2]octane cation

DETAILED DESCRIPTION

In practice, Zn-SSZ-42 is prepared by a process comprising:

(a) preparing an aqueous mixture containing sources of silicon oxide, zinc oxide, an alkali metal, and an N-benzyl-1,4-diazabicyclo[2.2.2]octane cation having an anionic counterion which is not detrimental to the formation of Zn-SSZ-42;

(b) maintaining the aqueous mixture under conditions sufficient to form crystals of Zn-SSZ-42; and (c) recovering the crystals of Zn-SSZ-42.

In preparing Zn-SSZ-42, a N-benzyl-1,4-diazabicyclo[2.2.2]octane cation (referred to herein as "benzyl DABCO") is used as a structure directing agent ("SDA"), also known as a crystallization template. This SDA useful for making Zn-SSZ-42 has the following structure:

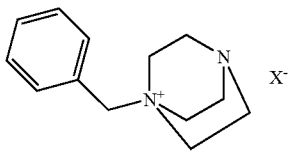

The SDA cation is associated with an anion ($X^-$) which may be any anion that is not detrimental to the formation of the molecular sieve. Representative anions include halogen, e.g., fluoride, chloride, bromide and iodide, hydroxide, acetate, sulfate, tetrafluoroborate, carboxylate, and the like. Hydroxide is the most preferred anion.

Benzyl DABCO and a method for making it are disclosed in U.S. Pat. No. 5,653,956, issued Aug. 5, 1997 to Zones.

Zn-SSZ-42 is prepared from a reaction mixture having the composition shown in Table A below.

TABLE A

| | Reaction Mixture | |
|---|---|---|
| | Typical | Preferred |
| $YO_2/ZnO$ | >10 | 15-100 |
| $OH^-/YO_2$ | 0.10-0.50 | 0.20-0.40 |
| $Q/YO_2$ | 0.05-0.50 | 0.10-0.40 |
| $M_{2/n}/YO_2$ | 0-0.40 | 0.01-0.25 |
| $H_2O/YO_2$ | 10-200 | 15-60 | where Y is silicon, germanium or a mixture thereof; M is an alkali metal cation, alkaline earth metal cation or mixtures thereof; n is the valence of M (i.e., 1 or 2); and a is a N-benzyl-1,4-diazabicyclo[2.2.2]octane cation, Zn-SSZ-42 as prepared has a mole ratio of an oxide selected from silicon oxide, germanium oxide and mixtures thereof to zinc oxide greater than about 10. Zn-SSZ-42 further has a composition, as synthesized (i.e., prior to calcination of Zn-SSZ-42) and in the anhydrous state, in terms of mole ratios, shown in Table B below.

TABLE B

| As-Synthesized Zn-SSZ-42 | |
|---|---|
| $YO_2/ZnO$ | 10-200 |
| $M_{2/n}/YO_2$ | 0-0.03 |
| $Q/YO_2$ | 0.02-0.05 | where Y, M, n and Q are as defined above.

Typical sources of silicon oxide include silicates, silica hydrogel, silicic acid, fumed silica, colloidal silica, tetraalkyl orthosilicates, and silica hydroxides. Typical sources of zinc oxide include water-soluble zinc salts, such as zinc acetate.

The reaction mixture is maintained at an elevated temperature until the crystals of the Zn-SSZ-42 molecular sieve are formed. The hydrothermal crystallization is usually conducted under autogenous pressure, at about 150° C. The crystallization period is typically greater than 1 day to about 30 days or more.

During the hydrothermal crystallization step, the Zn-SSZ-42 crystals can be allowed to nucleate spontaneously from the reaction mixture. The use of crystals of SSZ-42 (e.g., Zn-SSZ-42) as seed material can be advantageous in decreasing the time necessary for complete crystallization to occur. In addition, seeding can lead to an increased purity of the product obtained by promoting the nucleation and/or formation of Zn-SSZ-42 over any undesired phases. When used as seeds, as-synthesized Zn-SSZ-42 or Zn-SSZ-71 crystals are added in an amount between 0.1 and 10% of the weight of silica used in the reaction mixture. The molecular sieve designated SSZ-71 is disclosed in U.S. Pat. No. 7,083,776 issued Aug. 1, 2006 to Chen et al., which is incorporated by reference herein in its entirety.

Once the molecular sieve crystals have formed, the solid product is separated from the reaction mixture by standard mechanical separation techniques such as filtration. The crystals are water-washed and then dried, e.g., at ambient conditions or at elevated temperatures of about 90°C. to 150° C. for from 8 to 24 hours, to obtain the as-synthesized Zn-SSZ-42 molecular sieve crystals. The drying step can be performed at atmospheric pressure or under vacuum, Once the Zn-SSZ-42 crystals have been formed and recovered, the SDA should be removed. This is typically done by calcining the crystals at high temperature until the SDA is removed.

When used in a catalyst, the molecular sieve can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired.

Metals may also be introduced into the molecular sieve by replacing some of the cations in the molecular sieve with metal cations via standard ion exchange techniques (see, for example, U.S. Pat. No. 3,140,249 issued Jul. 7, 1964 to Plank et al.; U.S. Pat. No. 3,140,251 issued Jul. 7, 1964 to Plank et al.; and U.S. Pat. No. 3,140,253 issued Jul. 7, 1964 to Plank et al.). Typical replacing cations can include the following metal cations as well as their mixtures:

(1) Group IA: Li, Na, K, Rb, Cs
(2) Group IIA: Mg, Ca, Sr, Ba
(3) Group IVB: Ti, Zr
(4) Group VB: V, Nb
(5) Group VIB: Cr, No, W
(6) Group VIIB: Mn, Re
(7) Group VIII: Fe, Ru, Os, Co, Rh, Ir, Ni, Pd, Pt
(8) Group IB: Cu, Ag, Au
(9) Group IIB: Zn, Gd, Hg
(10) Group IIIA: Ga, In
(11) Group IVA: Ge, Sn, Pb When used in this disclosure, the Periodic Table of the Elements referred to is the version published by the CRC Press, Inc. In the CRC Handbook of Chemistry and Physics, 75th Edition (1994-1995). The numbering system used by Chemical Abstracts Service (CAS) is employed.

Of the replacing metallic cations, cations of metals such as rare earth, Mn, Ca, Mg, Zn, Cd, Pt, Pd, Ni, W, Co, Ti, Al, Sn, and Fe are particularly preferred.

The hydrogen, ammonium, and metal components can be ion-exchanged into the catalytically active Zn-SSZ-42. The molecular sieve can also be impregnated with the metals, or, the metals can be physically and intimately admixed with the molecular sieve using standard methods known to the art.

Typical ion-exchange techniques involve contacting the synthetic molecular sieve with a solution containing a salt of the desired replacing cation or cations. Although a wide variety of salts can be employed, chlorides and other halides, acetates, nitrates, and sulfates are particularly preferred. The molecular sieve is usually calcined prior to the ion-exchange procedure to remove the organic matter present in the channels and on the surface, since this results in a more effective ion exchange. Representative ion exchange techniques are disclosed in a wide variety of patents including U.S. Pat. No. 3,140,249 issued on Jul. 7, 1964 to Plank et al.; U.S. Pat. No. 3,140,251 issued on Jul. 7, 1964 to Plank et al.; and U.S. Pat. No. 3,140,253 issued on Jul. 7, 1964 to Plank et al.

Following contact with the salt solution of the desired replacing cation, the molecular sieve is typically washed with water and dried at temperatures ranging from 65° C. to about 200° C. After washing, the molecular sieve can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of Zn-SSZ-42, the spatial arrangement of the atoms which form the basic crystal lattice of the molecular sieve remains essentially unchanged.

Catalytically active Zn-SSZ-42 can be formed into a wide variety of physical shapes. Generally speaking, the molecular sieve can be in the form of a powder, a granule, or a molded products such as extrudate having a particle size sufficient to pass through a 2-mesh (Tyler) screen and be retained on a 400-mesh (Tyler) screen. In cases where the catalyst is molded, such as by extrusion with an organic binder, the molecular sieve can be extruded before drying, or, dried or partially dried and then extruded.

Catalytically active Zn-SSZ-42 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

Hydrocarbon Conversion Processes

Zn-SSZ-42 zeolites are useful in hydrocarbon conversion reactions. Hydrocarbon conversion reactions are chemical and catalytic processes in which carbon containing compounds are changed to different carbon containing compounds. Examples of hydrocarbon conversion reactions in which Zn-SSZ-42 are expected to be useful include hydrocracking, dewaxing, catalytic cracking and olefin and aromatics formation reactions. The catalysts are also expected to be useful in other petroleum refining and hydrocarbon conversion reactions such as isomerizing n-paraffins and naphthenes, polymerizing and oligomerizing olefinic or acetylenic compounds such as isobutylene and butene-1, polymerization of 1-olefins (e.g., ethylene), reforming, isomerizing polyalkyl substituted aromatics (e.g., m-xylene), and disproportionating aromatics (e.g., toluene) to provide mixtures of benzene, xylenes and higher methylbenzenes and oxidation reactions. Also included are rearrangement reactions to make various naphthalene derivatives, and forming higher molecular weight hydrocarbons from lower molecular weight hydrocarbons (e.g., methane upgrading).

The Zn-SSZ-42 catalysts may have high selectivity, and under hydrocarbon conversion conditions can provide a high percentage of desired products relative to total products.

For high catalytic activity, the Zn-SSZ-42 zeolite should be predominantly in its hydrogen ion form. Generally, the zeolite is converted to its hydrogen form by ammonium exchange followed by calcination. If the zeolite is synthesized with a high enough ratio of SDA cation to sodium ion, calcination alone may be sufficient. It is preferred that, after calcination, at least 80% of the cation sites are occupied by hydrogen ions and/or rare earth ions. As used herein, "predominantly in the hydrogen form" means that, after calcination, at least 80% of the cation sites are occupied by hydrogen ions and/or rare earth ions. Zn-SSZ-42 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil synthetic paraffins from NAO (normal alpha olefins), recycled plastic feedstocks and, in general, can be any carbon containing feedstocks susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reaction which can be performed using the catalyst of this invention containing a metal, e.g., a Group VIII metal such platinum, include hydrogenation-dehydrogenation reactions, denitrogenation and desulfurization reactions.

The following table indicates typical reaction conditions which may be employed when using catalysts comprising Zn-SSZ-42 in the hydrocarbon conversion reactions of this invention. Preferred conditions are indicated in parentheses.

| Process | Temp., ° C. | Pressure | LHSV |
|---|---|---|---|
| Hydrocracking | 175-485 | 0.5-350 bar | 0.1-30 |
| Dewaxing | 200-475 (250-450) | 15-3000 psig, 0.103-20.7 Mpa gauge (200-3000, 1.38-20.7 Mpa gauge) | 0.1-20 (0.2-10) |
| Aromatics formation | 400-600 (480-550) | atm.-10 bar | 0.1-15 |
| Cat. Cracking | 127-885 | subatm.-$^1$ (atm.-5 atm.) | 0.5-50 |
| Oligomerization | 232-649$^2$ 10-232$^4$ (27-204)$^4$ | 0.1-50 atm.$^{2,3}$ — — | 0.2-50$^2$ 0.05-20$^5$ (0.1-10)$^5$ |

-continued

| Process | Temp., °C. | Pressure | LHSV |
|---|---|---|---|
| Paraffins to aromatics | 100-700 | 0-1000 psig | 0.5-40[5] |
| Condensation of alcohols | 260-538 | 0.5-1000 psig, 0.00345-6.89 Mpa gauge | 0.5-50[5] |
| Isomerization | 93-538 (204-315) | 50-1000 psig, 0.345-6.89 Mpa gauge | 1-10 (1-4) |
| Xylene isomerization | 260-593[2] (315-566)[2] 38-371[4] | 0.5-50 atm.[2] (1-5 atm)[2] 1-200 atm.[4] | 0.1-100[5] (0.5-50)[5] 0.5-50 |

[1]Several hundred atmospheres
[2]Gas phase reaction
[3]Hydrocarbon partial pressure
[4]Liquid phase reaction
[5]WHSV Other reaction conditions and parameters are provided below.

Hydrocracking

Using a catalyst which comprises Zn-SSZ-42, preferably predominantly in the hydrogen form, and a hydrogenation promoter, heavy petroleum residual feedstocks, cyclic stocks and other hydrocrackate charge stocks can be hydrocracked using the process conditions and catalyst components disclosed in the aforementioned U.S. Pat. No. 4,910,006 and U.S. Pat. No. 5,316,753.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of nickel, platinum, palladium, cobalt, rhodium, iridium, ruthenium and mixtures thereof or the group consisting of at least one of chromium, molybdenum, tungsten, titanium and mixtures thereof. Reference to the catalytically active metal or metals is intended to encompass such metal or metals in the elemental state or in some form such as an oxide, sulfide, halide, carboxylate and the like. The hydrogenation catalyst is present in an effective amount to provide the hydrogenation function of the hydrocracking catalyst, and preferably in the range of from 0.05 to 25% by weight in the elemental state.

Dewaxing

Zn-SSZ-42, preferably predominantly in the hydrogen form, can be used to dewax hydrocarbonaceous feeds by selectively removing straight chain paraffins. Typically, the viscosity index of the dewaxed product is improved (compared to the waxy feed) when the waxy feed is contacted with Zn-SSZ-42 under isomerization dewaxing conditions.

The catalytic dewaxing conditions are dependent in large measure on the feed used and upon the desired pour point. Hydrogen is preferably present in the reaction zone during the catalytic dewaxing process The hydrogen to feed ratio is typically between about 500 and about 30,000 SCF/bbl (standard cubic feet per barrel) (0.089 to 5.34 SCM/liter (standard cubic meters/liter)), preferably about 1000 to about 20,000 SCF/bbl (0.178 to 3.56 SCM/liter). Generally, hydrogen will be separated from the product and recycled to the reaction zone. Typical feedstocks include light gas oil, heavy gas oils and reduced crudes boiling above about 350° F. (177° C.).

A typical dewaxing process is the catalytic dewaxing of a hydrocarbon oil feedstock boiling above about 350° F. (177° C.) and containing straight chain and slightly branched chain hydrocarbons by contacting the hydrocarbon oil feedstock in the presence of added hydrogen gas at a hydrogen pressure of about 15-3000 psi (0.103-20.7 Mpa) with a catalyst comprising Zn-SSZ-42 and at least one Group VIII metal.

The Zn-SSZ-42 hydrodewaxing catalyst may optionally contain a hydrogenation component of the type commonly employed in dewaxing catalysts. See the aforementioned U.S. Pat. No. 4,910,006 and U.S. Pat. No. 5,316,753 for examples of these hydrogenation components.

The hydrogenation component is present in an effective amount to provide an effective hydrodewaxing and hydroisomerization catalyst preferably in the range of from about 0.05 to 5% by weight in the elemental state of the hydrogenation metal(s). The catalyst may be run in such a mode to increase isomerization dewaxing at the expense of cracking reactions.

The feed may be hydrocracked, followed by dewaxing. This type of two stage process and typical hydrocracking conditions are described in U.S. Pat. No. 4,921,594, issued May 1, 1990 to Miller, which is incorporated herein by reference in its entirety.

Zn-SSZ-42 may also be utilized as a dewaxing catalyst in the form of a layered catalyst. That is, the catalyst comprises a first layer comprising zeolite Zn-SSZ-42 and at least one Group VIII metal, and a second layer comprising an aluminosilicate zeolite which is more shape selective than zeolite Zn-SSZ-42. The use of layered catalysts is disclosed in U.S. Pat. No. 5,149,421, issued Sep. 22, 1992 to Miller, which is incorporated by reference herein in its entirety. The layering may also include a bed of Zn-SSZ-42 layered with a non-zeolitic component designed for either hydrocracking or hydrofinishing.

Zn-SSZ-42 may also be used to dewax raffinates, including bright stock, under conditions such as those disclosed in U.S. Pat. No. 4,181,598, issued Jan. 1, 1980 to Gillespie et al., which is incorporated by reference herein in its entirety.

It is often desirable to use mild hydrogenation (sometimes referred to as hydrofinishing) to produce more stable dewaxed products. The hydrofinishing step can be performed either before or after the dewaxing step, and preferably after. Hydrofinishing is typically conducted at temperatures ranging from about 190° C. to about 340° C. at pressures from about 400 psig to about 3000 psig (2.76 to 20.7 Mpa gauge) at space velocities (LHSV) between about 0.1 and 20 and a hydrogen rate of about 400 to 1500 SCF/bbl (0.071 to 0.27 SCM/liter). The hydrogenation catalyst employed must be active enough not only to hydrogenate the olefins, diolefins and color bodies which may be present, but also to reduce the aromatic, content. Suitable hydrogenation catalyst are disclosed in U.S. Pat. No. 4,921,594, issued May 1, 1990 to Miller, which is incorporated by reference herein in its entirety. The hydrofinishing step is beneficial in preparing an acceptably stable product (e.g., a lubricating oil) since dewaxed products prepared from hydrocracked stocks tend to be unstable to air and light and tend to form sludges spontaneously and quickly.

Lube oil may be prepared using Zn-SSZ-42. For example, a $C_{20+}$ lube oil may be made by isomerizing a $C_{20+}$ feed over a catalyst comprising Zn-SSZ-42 in the hydrogen form and at least one Group VIII metal. Alternatively, the lubricating oil may be made by hydrocracking in a hydrocracking zone a hydrocarbonaceous feedstock to obtain an effluent comprising a hydrocracked oil, and catalytically dewaxing the effluent at a temperature of at least about 400° F. (204° C.) and at a pressure of from about 15 psig to about 3000 psig (0.103-20.7 Mpa gauge) in the presence of added hydrogen gas with a catalyst comprising Zn-SSZ-42 in the hydrogen form and at least one Group VIII metal.

Aromatics Formation

Zn-SSZ-42 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with a catalyst comprising Zn-SSZ-42. It is also possible to convert heavier feeds into BTX (benzene, toluene, xylenes and ethylbenzene) or naphthalene derivatives of value using a catalyst comprising Zn-SSZ-42.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium, tin or germanium or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

It is critical to the selective production of aromatics in useful quantities that the conversion catalyst be substantially free of acidity, for example, by neutralizing the zeolite with a basic metal, e.g. alkali metal, compound. Methods for rendering the catalyst free of acidity are known in the art. See the aforementioned U.S. Pat. No. 4,910,006 and U.S. Pat. No. 5,316,753 for a description of such methods.

The preferred alkali metals are lithium, sodium, potassium, rubidium and cesium. The zeolite itself can be substantially free of acidity only at very high silica contents.

Catalytic Cracking

Hydrocarbon cracking stocks can be catalytically cracked in the absence of hydrogen using Zn-SSZ-42, preferably predominantly in the hydrogen form.

When Zn-SSZ-42 is used as a catalytic cracking catalyst in the absence of hydrogen, the catalyst may be employed in conjunction with traditional cracking catalysts, e.g., any aluminosilicate heretofore employed as a component in cracking catalysts. Typically, these are large pore, crystalline aluminosilicates. Examples of these traditional cracking catalysts are disclosed in the aforementioned U.S. Pat. No. 4,910,006 and U.S. Pat. No. 5,316,753. When a traditional cracking catalyst (TC) component is employed, the relative weight ratio of the TC to the Zn-SSZ-42 is generally between about 1:10 and about 500:1, desirably between about 1:10 and about 200:1, preferably between about 1:2 and about 50:1, and most preferably is between about 1:1 and about 20:1. The Zn-SSZ-42 zeolite and/or the traditional cracking component may be further ion exchanged with rare earth ions to modify selectivity.

The cracking catalysts are typically employed with an inorganic oxide matrix component. See the aforementioned U.S. Pat. No. 4,910,006 and U.S. Pat. No. 5,316,753 for examples of such matrix components.

Isomerization of Paraffins

The present catalyst is highly active and highly selective for isomerizing $C_4$ to $C_7$ hydrocarbons. The activity means that the catalyst can operate at relatively low temperature which thermodynamically favors highly branched paraffins. Consequently, the catalyst can produce a high octane product The high selectivity means that a relatively high liquid yield can be achieved when the catalyst is run at a high octane.

The present process comprises contacting the isomerization catalyst, i.e., a catalyst comprising Zn-SSZ-42 in the hydrogen form with a hydrocarbon feed under isomerization conditions. The feed is preferably a light straight run fraction, boiling within the range of 30° F. to 250° F. (−1° C. to 121° C.) and preferably from 60° F. to 200° F. (16° C. to 93° C.) Preferably, the hydrocarbon feed for the process comprises a substantial amount of $C_4$ to $C_7$ normal and slightly branched low octane hydrocarbons more preferably $C_5$ and $C_6$ hydrocarbons.

It is preferable to carry out the isomerization reaction in the presence of hydrogen. Preferably, hydrogen is added to give a hydrogen to hydrocarbon molar ratio ($H_2$/HC) of between 0.5 and 10 $H_2$/HC, more preferably between 1 and 8 $H_2$/HC. See the aforementioned U.S. Pat. No 4,910,006 and U.S. Pat. No. 5,316,753 for a further discussion of isomerization process conditions.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrotreating the feed in a pre-hydrotreating zone with a hydrotreating catalyst which is resistant to sulfur poisoning. See the aforementioned U.S. Pat. No. 4,910,006 and U.S. Pat. No. 5,316,753 for a further discussion of this hydrodesulfurization process.

It is preferable to limit the nitrogen level and the water content of the feed. Catalysts and processes which are suitable for these purposes are known to those skilled in the art.

After a period of operation, the catalyst can become deactivated by sulfur or coke. See the aforementioned U.S. Pat. No. 4,910,006 and U.S. Pat. No. 5,316,753 for a further discussion of methods of removing this sulfur and coke, and of regenerating the catalyst.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium, germanium and tin may also be used in conjunction with the noble metal. The most preferred metal is platinum. The amount of Group VIII metal present in the conversion catalyst should be within the normal range of use in isomerizing catalysts, from about 0.05 to 2.0 weight percent, preferably 0.2 to 0.8 weight percent.

Alkylation and Transalkylation of Aromatics

Zn-SSZ-42 can be used in a process for the alkylation or transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial liquid phase conditions, and in the presence of a catalyst comprising Zn-SSZ-42.

Zn-SSZ-42 can also be used for removing benzene from gasoline by alkylating the benzene as described above and removing the alkylated product from the gasoline.

For high catalytic activity, the Zn-SSZ-42 zeolite should be predominantly in its hydrogen ion form. It is preferred that after calcination, at least 80% of the cation sites are occupied by hydrogen ions and/or rare earth ions.

Examples of suitable aromatic hydrocarbon feed stocks which may be alkylated or transalkylated by the process of the invention include aromatic compounds such as benzene, toluene and xylene. The preferred aromatic hydrocarbon is benzene. There may be occasions where naphthalene or naphthalene derivatives such as dimethylnaphthalene may be desirable. Mixtures of aromatic hydrocarbons may also be employed.

Suitable olefins for the alkylation of the aromatic hydrocarbon are those containing 2 to 20, preferably 2 to 4, carbon atoms, such as ethylene, propylene, butene-1, trans-butene-2 and cis-butene-2, or mixtures thereof. There may be instances where pentenes are desirable. The preferred olefins are ethylene and propylene. Longer chain alpha olefins may be used as well.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene) di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

When alkylation is the process conducted reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100° F. to 600° F. (38° C. to 315° C.), preferably 250° F. to 450° F. (121° C. to 232° C.). The reaction pressure should be sufficient to maintain at least a partial liquid phase in order to retard catalyst fouling. This is typically 50 psig to 1000 psig (0.345 to 6.89 Mpa gauge) depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbons will generally range from about 1:1 to 25:1, and preferably from about 2:1 to 20:1. The reaction temperature may range from about 100° F. to 600° F. (38° C. to 315° C.), but it is preferably about 250° F. to 450° F. (121° C. to 232° C.). The reaction pressure should be sufficient to maintain at least a partial liquid phase, typically in the range of about 50 psig to 1000 psig (0.345 to 6.89 Mpa gauge), preferably 300 psig to 600 psig (2.07 to 4.14 Mpa gauge). The weight hourly space velocity will range from about 0.1 to 10. U.S. Pat. No. 5,082,990 issued on Jan. 21, 1992 to Hsieh, et al. describes such processes and is incorporated herein by reference.

Conversion of Light Paraffins to Aromatics

Zn-SSZ-42 can be used to convert light gas $C_2$-$C_6$ paraffins to higher molecular weight hydrocarbons including aromatic compounds. Preferably, the zeolite will contain a catalyst metal or metal oxide wherein said metal is selected from the group consisting of Groups IB, IIB, VIII and IIIA of the Periodic Table. Preferably, the metal is gallium, niobium, indium or zinc in the range of from about 0.05 to 5% by weight.

Isomerization of Olefins

Zn-SSZ42 can be used to isomerize olefins. The feed stream is a hydrocarbon stream containing at least one $C_{4-6}$ olefin, preferably a $C_{4-6}$ normal olefin, more preferably normal butene. Normal butene as used in this specification means all forms of normal butene, e.g., 1-butene, cis-2-butene, and trans-2-butene. Typically, hydrocarbons other than normal butene or other $C_{4-6}$ normal olefins will be present in the feed stream. These other hydrocarbons may include, e.g., paraffins, other olefins, diolefins, naphthenes, aromatics, hydrogen, and inert gases.

The feed stream typically may be the effluent from a fluid catalytic cracking unit or a methyl-tert-butyl ether unit. A fluid catalytic cracking unit effluent typically contains about 40-60 weight percent normal butenes. A methyl-tert-butyl ether unit effluent typically contains 40-100 weight percent normal butene. The feed stream preferably contains at least about 40 weight percent normal butene, more preferably at least about 65 weight percent normal butene. The terms iso-olefin and methyl branched iso-olefin may be used interchangeably in this specification.

The process is carried out under isomerization conditions. The hydrocarbon feed is contacted in a vapor phase with a catalyst comprising the Zn-SSZ-42. The process may be carried out generally at a temperature from about 625° F. to about 950° F. (329-510° C.), for butenes, preferably from about 700° F. to about 900° F. (371-482° C.), and about 350° F. to about 650° F. (177-343° C.) for pentenes and hexenes. The pressure ranges from subatmospheric to about 200 psig (1.38 Mpa gauge), preferably from about 15 psig to about 200 psig (0.103 to 1.38 Mpa gauge), and more preferably from about 1 psig to about 150 psig (0.00689 to 1.03 Mpa gauge)

The liquid hourly space velocity during contacting is generally from about 0.1 to about 50 $hr^{-1}$, based on the hydrocarbon feed, preferably from about 0.1 to about 20 $hr^{-1}$, more preferably from about 0.2 to about 10 $hr^{-1}$, most preferably from about 1 to about 5 $hr^{-1}$. A hydrogen/hydrocarbon molar ratio is maintained from about 0 to about 30 or higher. The hydrogen can be added directly to the feed stream or directly to the isomerization zone. The reaction is preferably substantially free of water, typically less than about two weight percent based on the feed. The process can be carried out in a packed bed reactor, a fixed bed, fluidized bed reactor, or a moving bed reactor. The bed of the catalyst can move upward or downward. The mole percent conversion of, e.g., normal butene to iso-butene is at least 10, preferably at least 25, and more preferably at least 35.

Xylene Isomerization

Zn-SSZ-42 may also be useful in a process for isomerizing one or more xylene isomers in a $C_8$ aromatic feed to obtain ortho-, meta-, and para-xylene in a ratio approaching the equilibrium value. In particular, xylene isomerization is used in conjunction with a separate process to manufacture para-xylene. For example, a portion of the para-xylene in a mixed $C_8$ aromatics stream may be recovered by crystallization and centrifugation. The mother liquor from the crystallizer is then reacted under xylene isomerization conditions to restore ortho-, meta- and para-xylenes to a near equilibrium ratio. At the same time, part of the ethylbenzene in the mother liquor is converted to xylenes or to products which are easily separated by filtration. The isomerate is blended with fresh feed and the combined stream is distilled to remove heavy and light byproducts. The resultant $C_8$ aromatic s stream is then sent to the crystallizer to repeat the cycle.

Optionally, isomerization in the vapor phase is conducted in the presence of 3.0 to 30.0 moles of hydrogen per mole of alkylbenzene (e.g., ethylbenzene). If hydrogen is used, the catalyst should comprise about 0.1 to 2.0 wt. % of a hydrogenation/dehydrogenation component selected from Group VIII (of the Periodic Table) metal component, especially platinum or nickel. By Group VIII metal component is meant the metals and their compounds such as oxides and sulfides.

Optionally, the isomerization feed may contain 10 to 90 wt. of a diluent such, as toluene, trimethylbenzene, naphthenes or paraffins.

Oligomerization

It is expected that Zn-SSZ-42 can also be used to oligomerize straight and branched chain olefins having from about 2 to 21 and preferably 2-5 carbon atoms. The oligomers which are the products of the process are medium to heavy olefins which are useful for fuels, i.e., gasoline or a gasoline blending stock, jet/diesel or a jet/diesel blending stockand chemicals.

The oligomerization process comprises contacting the olefin feedstock in the gaseous or liquid phase with a catalyst comprising Zn-SSZ-42.

The zeolite can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group IIB; of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20% by weight. This is accomplished by using a zeolite with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens et al, which is incorporated totally herein by reference. If required, such zeolites may be obtained by steaming, by use in a conversion process or by any other method which may occur to one skilled in this art.

Condensation of Alcohols

Zn-SSZ-42 can be used to condense lower aliphatic alcohols having 1 to 10 carbon atoms to a gasoline boiling point hydrocarbon product comprising mixed aliphatic and aromatic hydrocarbon. The process disclosed in U.S. Pat. No. 3,894,107, issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups IA through VIII of the Periodic Table. However, in the case of Group IA metals, the cation content should in no case be so large as to effectively inactivate the catalyst, nor should the exchange be such as to eliminate all acidity. There may be other processes involving treatment of oxygenated substrates where a basic catalyst is desired.

Methane Upgrading

Higher molecular weight hydrocarbons can be formed from lower molecular weight hydrocarbons by contacting the lower molecular weight hydrocarbon with a catalyst comprising Zn-SSZ-42 and a metal or metal compound capable of converting the lower molecular weight hydrocarbon to a higher molecular weight hydrocarbon. Examples of such reactions include the conversion of methane to $C_{2+}$ hydrocarbons such as ethylene or benzene or both. Examples of useful metals and metal compounds include lanthanide and or actinide metals or metal compounds.

These reactions, the metals or metal compounds employed and the conditions under which they can be run are disclosed in. U.S. Pat. No. 4,734,537, issued Mar. 29, 1988 to Devries et al.; U.S. Pat. No. 4,939,311, issued Jul. 3, 1990 to Washecheck et al.; U.S. Pat. No. 4,962,261, issued Oct. 9, 1990 to Abrevaya et al.; U.S. Pat. No. 5,095,161, issued Mar. 10, 1992 to Abrevaya et al.; U.S. Pat. No. 5,105,044, issued Apr. 14, 1992 to Han et al.; U.S. Pat. No. 5,105,046, issued Apr. 14, 1992 to Washecheck; U.S. Pat. No. 5,238,898, issued Aug. 24, 1993 to Han et al.; U.S. Pat. No. 5,321,185, issued Jun. 14, 1994 to van der Vaart; and U.S. Pat. No. 5,336,825, issued Aug. 9, 1994 to Choudhary et al., each of which is incorporated herein by reference in its entirety.

Polymerization of 1-Olefins

The molecular sieve of the present invention may be used in a catalyst for the polymerization of 1-olefins, e.g., the polymerization of ethylene. To form the olefin polymerization catalyst, the molecular sieve as hereinbefore described is reacted with a particular type of organometallic compound. Organometallic compounds useful in forming the polymerization catalyst include trivalent and tetravalent organotitanium and organochromium compounds having alkyl moieties and, optionally, halo moieties. In the context of the present invention the term "alkyl" includes both straight and branched chain alkyl, cycloalkyl and alkylaryl groups such as benzyl.

Examples of trivalent and tetravalent organochromium and organotitanium compounds are disclosed in U.S. Pat. No. 4,376,722, issued Mar. 15, 1983 to Chester et al., U.S. Pat. No. 4,377,497, issued Mar. 22, 1983 to Chester et al., U.S. Pat. No. 4,446,243, issued May 1, 1984 to Chester et al., and U.S. Pat. No. 4,526,942, issued Jul. 2, 1985 to Chester et al. The aforementioned patents are incorporated herein by reference in their entirety.

Examples of the organometallic compounds used to form the polymerization catalyst include, but are not limited to, compounds corresponding to the general formula:

$$MY_nX_{m-n}$$

wherein M is a metal selected from titanium and chromium; Y is alkyl; X is halogen (e.g., Cl or Br); n is 1-4; and m is greater than or equal to n and is 3 or 4.

Examples of organotitanium and organochromium compounds encompassed by such a formula include compounds of the formula $CrY_4$, $CrY_3$, $CrY_3X$, $CrY_2X$, $CrY_2X_2$, $CrYX_2$, $CrYX_3$, $TiY_4$, $TiY_3$, $TiY_3X$, $TiY_2X$, $TiY_2X_2$, $TiYX_2$, $TiYX_3$, wherein X can be Cl or Br and Y can be methyl, ethyl, propyl, isopropyl, butyl, isobutyl, sec-butyl, tert-butyl, pentyl, isopentyl, neopentyl, hexyl, isohexyl, neohexyl, 2-ethybutyl, octyl, 2-ethylhexyl, 2,2-diethylbutyl, 2-isopropyl-3-methylbutyl, etc., cyclohexylalkyls such as, for example, cyclohexylmethyl, 2-cyclohexylethyl, 3-cyclyhexylpropyl, 4-cyclohexylbutyl, and the corresponding alkyl-substituted cyclohexyl radicals as, for example, (4-methylcyclohexyl) methyl, neophyl, i.e., beta, beta-dimethyl-phenethyl, benzyl, ethylbenzyl, and p-isopropylbenzyl. Preferred examples of Y include $C_{1-5}$ alkyl, especially butyl.

The organotitanium and organochromium materials employed in the catalyst can be prepared by techniques well known in the art. See, for example the aforementioned Chester et al. patents.

The organotitanium or organochromium compounds can be with the molecular sieve of the present invention, such as by reacting the organometallic compound and the molecular sieve, in order to form the olefin polymerization catalyst. Generally, such a reaction takes place in the same reaction medium used to prepare the organometallic compound under conditions which promote formation of such a reaction product. The molecular sieve can simply be added to the reaction mixture after formation of the organometallic compound has been completed. Molecular sieve is added in an amount sufficient to provide from about 0.1 to 10 parts by weight, preferably from about 0.5 to 5 parts by weight, of organometallic compound in the reaction medium per 100 parts by weight of molecular sieve.

Temperature of the reaction medium during reaction of organometallic compound with molecular sieve is also maintained at a level which is low enough to ensure the stability of the organometallic reactant. Thus, temperatures in the range of from about −150° C. to 50° C., preferably from about −80° C. to 0° C. can be usefully employed. Reaction times of from about 0.01 to 10 hours, more preferably from about 0.1 to 1 hour, can be employed in reacting the organotitanium or organochromium compound with the molecular sieve.

Upon completion of the reaction, the catalyst material so formed may be recovered and dried by evaporating the reaction medium solvent under a nitrogen atmosphere. Alternatively, olefin polymerization reactions can be conducted in this same solvent based reaction medium used to form the catalyst.

The polymerization catalyst can be used to catalyze polymerization of 1-olefins. The polymers produced using the catalysts of this invention are normally solid polymers of at least one mono-1-olefin containing from 2 to 8 carbon atoms per molecule. These polymers are normally solid homopolymers of ethylene or copolymers of ethylene with another mono-1-olefin containing 3 to 8 carbon atoms per molecule. Exemplary copolymers include those of ethylene/propylene, ethylene/1-butene, ethylene/1-hexane, and ethylene/1-octene and the like. The major portion of such copolymers, is derived from ethylene and generally consists of about 80-99, preferably 95-99 mole percent of ethylene. These polymers are well suited for extrusion, blow molding, injection molding and the like.

The polymerization reaction can be conducted by contacting monomer or monomers, e.g., ethylene, alone or with one or more other olefins, and in the: substantial absence of catalyst poisons such as moisture and air, with a catalytic amount of the supported organometallic catalyst at a temperature and at a pressure sufficient to initiate the polymerization reaction. If desired, an inert organic solvent may be used as a diluent and to facilitate materials handling if the polymerization reaction is conducted with the reactants in the liquid phase, e.g. in a particle form (slurry) or solution process. The reaction may also be conducted with reactants in the vapor phase, e.g., in a fluidized bed arrangement in the absence of a solvent but, if desired, in the presence of an inert gas such as nitrogen.

The polymerization reaction is carried out at temperatures of from about 30° C. or less, up to about 200° C. or more, depending to a great extent on the operating pressure, the pressure of the olefin monomers, and the particular catalyst being used and its concentration. Naturally, the selected operating temperature is also dependent upon the desired polymer melt index since temperature is definitely a factor in adjusting the molecular weight of the polymer. Preferably, the temperature used is from about 30° C. to about 100° C. in a conventional slurry or "particle forming" process or from 100° C. to 150° C. in a "solution forming" process. A temperature of from about 70° C. to 110° C. can be employed for fluidized bed processes.

The pressure to be used in the polymerization reactions can be any pressure sufficient to initiate the polymerization of the monomer(s) to high molecular weight polymer. The pressure, therefore, can range from subatmospheric pressures, using an inert gas as diluent, to superatmospheric pressures of up to about 30,000 psig or more. The preferred pressure is from atmospheric (0 psig) up to about 1000 psig. As a general rule, a pressure of 20 to 800 psig is most preferred.

The selection of an inert organic solvent medium to be employed in the solution or slurry process embodiments of this invention is not too critical, but the solvent should be inert to the supported organometallic catalyst and olefin polymer produced, and be stable at the reaction temperature used. It is not necessary, however, that the inert organic solvent medium also serve as a solvent for the polymer to be produced. Among the inert organic solvents applicable for such purposes may be mentioned saturated aliphatic hydrocarbons having from about 3 to 12 carbon atoms per molecule such as hexane, heptane, pentane, isooctane, purified kerosene and the like, saturated cycloaliphatic hydrocarbons having from about 5 to 12 carbon atoms per molecule such as cyclohexane, cyclopentane, dimethylcyclopentane and methylcyclohexane and the like and aromatic hydrocarbons having from about 6 to 12 carbon atoms per molecule such as benzene, toluene, xylene, and the like. Particularly preferred solvent media are cyclohexane, pentane, hexane and heptane.

Hydrogen can be introduced into the polymerization reaction zone in order to decrease the molecular weight of the polymers produced (i.e., give a much higher Melt Index, MI). Partial pressure of hydrogen when hydrogen is used can be within the range of 5 to 100 psig, preferably 25 to 75 psig. The melt indices of the polymers produced in accordance with the instant invention can range from about 0.1 to about 70 or even higher.

More detailed description of suitable polymerization conditions including examples of particle form, solution and fluidized bed polymerization arrangements are found in U.S. Pat. No. 3,709,853, issued Jan. 9, 1973 to Karapinka, and U.S. Pat. No. 4,086,408, issued Apr. 25, 1978 to Karol et al. Both of these patents are incorporated herein by reference.

Hydrotreating

Zn-SSZ-42 is useful in a hydrotreating catalyst. During hydrotreatment, oxygen, sulfur and nitrogen present in the hydrocarbonaceous feed is reduced to low levels. Aromatics and olefins, if present in the feed, may also have their double bonds saturated. In some cases, the hydrotreating catalyst and hydrotreating conditions are selected to, minimize cracking reactions, which can reduce the yield of the most desulfided product (typically useful as a fuel).

Hydrotreating conditions typically include a reaction temperature between 400-900° F. (204-482° C.) preferably 650-850° F. (343-454° C.), a pressure between 500 and 5000 psig (3.5-34.6 Mpa), preferably 1000 to 3000 psig (7.0-20.8 MPa); a feed rate (LHSV) of 0.5 hr$^{-1}$ to 20 hr$^{-1}$ (v/v); and overall hydrogen consumption 300 to 4000 scf per barrel of liquid hydrocarbon feed (53.4-712 m$^3$ H$_2$/m$^3$ feed). The hydrotreating catalyst will typically be a composite of a Group VI metal or compound thereof, and a Group VIII metal or compound thereof supported on the molecular sieve of this invention. Typically, such hydrotreating catalyst are presulfided.

Catalysts useful for hydrotreating hydrocarbon feeds are disclosed in U.S. Pat. No. 4,347,121, issued Aug. 31, 1982 to Mayer et al, and U.S. Pat. No. 4,810,357, issued Mar. 7, 1989 to Chester et al, both of which are incorporated herein by reference in their entirety. Suitable catalysts include noble metals from Group VIII, such as Fe, Co, Ni, Pt or Pd, and/or Group VI metals, such as Cr, Mo or W and/or Group IVA metals such as Sn. Examples of combinations of Group VIII and Group VIB or Group IVA metals include Ni—Mo or Ni—Sn. Other suitable catalysts are described in U.S. Pat. No. 4,157,294 issued Jun. 5, 1979 to Iwao et al, and U.S. Pat. No. 3,904,513, issued Sep. 9, 1975 to Fischer et) al. U.S. Pat. No. 3,852,207, issued Dec. 3, 1974 to Strangeland et al, describes suitable noble metal catalysts and mild hydrotreating conditions. The contents of these patents are hereby incorporated by reference.

The amount of hydrogenation component(s) in the catalyst suitably range from about 0.5% to about 10% by weight of Group VIII component(s) and from 5% to about 25% by weight of Group VIB or IVA metal component(s), calculated as metal oxide(s) per the weight of total catalyst., where the percentages by weight are based on the weight of the catalyst before sulfiding. The hydrogenation component(s) in the catalyst may be in the oxidic and/or sulfidic form.

Hydrogenation

Zn-SSZ-42 can be used in a catalyst to catalyze hydrogenation of a hydrocarbon feed containing unsaturated hydrocarbons. The unsaturated hydrocarbons can comprise olefins, dienes, polyenes, aromatic compounds and the like.

Hydrogenation is accomplished by contacting the hydrocarbon feed containing unsaturated hydrocarbons with hydrogen in the presence of a catalyst comprising Zn-SSZ-42. The catalyst can also contain one or more metals of Group VIB and Group VIII, including salts, complexes and solutions thereof. Reference to these catalytically active metals is intended to encompass such metals or metals in the elemental state or in some form such as an oxide, sulfide, halide, carboxylate and the like. Examples of such metals include metals, salts or complexes wherein the metal is selected from the group consisting of platinum, palladium, rhodium, iridium or combinations thereof, or the group consisting of nickel, molybdenum, cobalt, tungsten, titanium, chromium, vanadium, rhenium, manganese and combinations thereof.

The hydrogenation component of the catalyst (i.e., the aforementioned metal) is present in an amount effective to provide the hydrogenation function of the catalyst, preferably in the range of from 0.05 to 25% by weight.

Hydrogenation conditions, such as temperature, pressure, space velocities, contact time and the like are well known in the art.

Zn-SSZ-42 may also be used for the catalytic reduction of the oxides of nitrogen in a gas stream. Typically, the gas stream also contains oxygen, often a stoichiometric excess thereof. Also, the Zn-SSZ-42 may contain a metal or metal ions within or on it which are capable of catalyzing the reduction of the nitrogen oxides. Examples of such metals or metal ions include copper, cobalt and mixtures thereof.

One example of such a process for the catalytic reduction of oxides of nitrogen in the presence of a molecular sieve is disclosed in U.S. Pat. No. 4,297,328, issued Oct. 27, 1981 to Ritscher et al., which is incorporated by reference herein. There, the catalytic process is the combustion of carbon monoxide and hydrocarbons and the catalytic reduction of the oxides of nitrogen contained in a gas stream, such as the exhaust gas from an internal combustion engine. The molecular sieve used is metal ion-exchanged, doped or loaded sufficiently so as to provide an effective amount of catalytic copper metal or copper ions within or on the molecular sieve. In addition, the process is conducted in an excess of oxidant, e.g., oxygen.

Dehydrogenation

Zn-SSZ-42 can be used in catalysts for the dehydrogenation of alkanes, particularly the dehydrogenation of propane. Dehydrogenation conditions, such as temperature, pressure, space velocities, contact time and the like are well known in the art.

Some experimental examples of the invention are given below. As represented by Example 1, the typical XRD data of the as synthesized Zn-SSZ-42 samples (i.e., Zn-SSZ-42 prior to removal of the SDA) of the present invention are given in Table 1.

EXAMPLE 1

846.4 g of aqueous 0.85 M N-benzyl-1,4-diazabicyclo [2.2.2]octane hydroxide solution was mixed with 1285.3 g of distilled water and 3.74 g of NaOH. Then 16.69 g of Zn(CH$_3$COO)$_2$.2H$_2$O was added and the resulting solution was stirred at room temperature overnight. Subsequently, 152.4 g of Cab-O-Sil M-5 fumed silica was blended to this solution and it was stirred at room temperature for 1 hour.

The above gel was transferred to an autoclave and heated at 150° C. first under stirring at 60 rpm for 8 days and then at 75 rpm for 5 days. Subsequently, 420 g of aqueous 0.85M N-benzyl-1,4-diazabicyclo [2.2.2]octane hydroxide solution was added to the synthesis medium and it was heated at 160° C. under stirring at 75 rpm for 2 days. Finally, the synthesis medium was heated at 175° C. for 3 days either under static conditions or under stirring at 75 rpm. The resulting solid product was recovered by filtration and washing with distilled water. It was then dried under ambient conditions. As listed in Table 1, the XRD data of the resulting solid product show the XRD pattern lines characteristic of zeolite SSZ-42.

TABLE 1

XRD Data of As-Synthesized Zn-SSZ-42 Prepared in Example 1

| Two Theta[a] | d-Spacing (Å) | Relative Intensity (%) |
|---|---|---|
| 8.13 | 10.87 | 60.9 |
| 9.61 | 9.20 | 6.4 |
| 13.52 | 6.54 | 12.2 |
| 15.16 | 5.84 | 2.6 |
| 15.88 | 5.58 | 5.7 |
| 16.32 | 5.43 | 10.7 |
| 18.95 | 4.68 | 22.7 |
| 19.30 | 4.60 | 3.6 |
| 20.40 | 4.35 | 100.0 |

TABLE 1-continued

XRD Data of As-Synthesized Zn-SSZ-42 Prepared in Example 1

| Two Theta[a] | d-Spacing (Å) | Relative Intensity (%) |
|---|---|---|
| 21.35 | 4.16 | 26.7 |
| 21.58 | 4.11 | 43.9 |
| 23.48 | 3.79 | 12.1 |
| 23.69 | 3.75 | 38.7 |
| 24.66 | 3.61 | 17.3 |
| 25.10 | 3.55 | 6.7 |
| 25.98 | 3.43 | 30.0 |
| 26.49 | 3.36 | 21.5 |
| 27.21 | 3.27 | 7.2 |
| 27.50 | 3.24 | 4.8 |
| 28.13 | 3.17 | 6.8 |
| 28.69 | 3.11 | 2.1 |
| 29.11 | 3.07 | 15.0 |
| 29.90 | 2.99 | 2.7 |
| 30.55 | 2.92 | 2.9 |
| 31.48 | 2.84 | 9.1 |
| 32.06 | 2.79 | 4.8 |
| 33.01 | 2.71 | 4.3 |
| 33.70 | 2.66 | 6.1 |
| 34.37 | 2.61 | 7.4 |
| 35.18 | 2.55 | 6.4 |
| 35.44 | 2.53 | 2.8 |
| 35.86 | 2.50 | 7.3 |
| 36.53 | 2.46 | 10.5 |

[a] ±0.15

EXAMPLE 2

4.25 g of aqueous 0.85 M N-benzyl-1,4-diazabicyclo[2,2.2]octane hydroxide solution was mixed with 6.5 g of distilled water and 0.019 g of NaOH. Then, 0.084 g of $Zn(CH_3COO)_2.2H_2O$ was added and the resulting solution was stirred at room temperature overnight. Subsequently, 0.76 g of Cab-O-Sil M-5 fumed silica was blended to this solution and it was stirred at room temperature for 1 hour. Finally, 0.015 g of as-synthesized Zn-SSZ-42 was added as seeds and the gel was stirred at room temperature for another 15 minutes.

The above gel was transferred to an autoclave and heated at 150° C. under static conditions for 8 days. The resulting solid product was recovered by filtration and washing with distilled water. It was then dried under ambient conditions. The resulting solid product shows the XRD pattern lines characteristic of zeolite SSZ-42.

EXAMPLE 3

4.25 g of aqueous 0.85 M N-benzyl-1,4-diazabicyclo[2.2.2]octane hydroxide solution was mixed with 6.5 g of distilled water and 0.019 g of NaOH. Then, 0.084 g of $Zn(CH_3COO)_2.2H_2O$ was added and the resulting solution was stirred at room temperature overnight. Subsequently, 0.76 g of Cab-O-Sil M-5 fumed silica was blended to this solution and it was stirred at room temperature for 1 hour. Finally, 0.015 g of as-synthesized Zn-SSZ-71 was added as seeds and the get was stirred at room temperature for another 15 minutes.

The above gel was transferred to an autoclave and heated at 150° C. under static conditions for 26 days. The resulting solid product was recovered by filtration and washing with distilled water. It was then dried under ambient conditions. The XRD data of the resulting solid product show the XRD pattern lines characteristic of zeolite SSZ-42.

What is claimed is:

1. A process for preparing a zinc-containing molecular sieve having IFR framework topology and having zinc atoms in its crystal framework, said process comprising:
    (a) preparing an aqueous mixture containing sources of (1) silicon oxide, germanium oxide or mixtures thereof; (2) zinc oxide; (3) an alkali metal, alkaline earth metal or mixtures thereof; and (4) an N-benzyl-1,4-diazabicyclo[2.2.2]octane cation having an anionic counterion which is not detrimental to the formation of the molecular sieve; and
    (b) maintaining the aqueous mixture under conditions sufficient to form crystals of the molecular sieve.

2. The process of claim 1 wherein the aqueous mixture comprises:

| | |
|---|---|
| $YO_2/ZnO$ | >10 |
| $OH^-/YO_2$ | 0.10-0.50 |
| $Q/YO_2$ | 0.05-0.50 |
| $M_{2/n}/YO_2$ | 0-0.40 |
| $H_2O/YO_2$ | 10-200 | where Y is silicon, germanium or a mixture thereof; M is an alkali metal cation, alkaline earth metal cation or mixtures thereof; n is the valence of M; and Q is a N-benzyl-1,4-diazabicyclo[2.2.2]octane cation.

3. The process of claim 2 wherein the aqueous mixture comprises:

| | |
|---|---|
| $YO_2/ZnO$ | 15-100 |
| $OH^-/YO_2$ | 0.20-0.40 |
| $Q/YO_2$ | 0.10-0.40 |
| $M_{2/n}/YO_2$ | 0.01-0.25 |
| $H_2O/YO_2$ | 15-60. |

4. A zinc-containing molecular sieve having IFR framework topology and having a compositions as synthesized and in the anhydrous state, in terms of mole ratios as follows:

| | |
|---|---|
| $YO_2/ZnO$ | 10-200 |
| $M_{2/n}/YO_2$ | 0-0.03 |
| $Q/YO_2$ | 0.02-0.05 | wherein Y is silicon, germanium or mixtures thereof; M is an alkali metal cation, alkaline earth metal cation or mixtures thereof; n is the valence of M; and Q is an N-benzyl-1,4-diazabicyclo[2.2.2]octane cation.

* * * * *